(12) United States Patent
Kapec et al.

(10) Patent No.: US 10,828,141 B2
(45) Date of Patent: *Nov. 10, 2020

(54) IMPLANT PACKAGING ASSEMBLY

(71) Applicant: Musculoskeletal Transplant Foundation, Edison, NJ (US)

(72) Inventors: Jeffrey Kapec, Westport, CT (US);
Jacob Turetsky, Brooklyn, NY (US);
Yukiko Naoi, New York, NY (US);
Alison Ling, Piscataway, NJ (US);
German Eduardo Jurado Rivera, Rahway, NJ (US); Darrin Friend, East Windsor, NJ (US); Morris Jacobs, Newton, PA (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/782,587

(22) Filed: Feb. 5, 2020

(65) Prior Publication Data

US 2020/0170772 A1    Jun. 4, 2020

Related U.S. Application Data

(62) Division of application No. 15/913,448, filed on Mar. 6, 2018, now Pat. No. 10,582,994.

(51) Int. Cl.
*A61F 2/00* (2006.01)
*B65D 75/32* (2006.01)
(Continued)

(52) U.S. Cl.
CPC ........ *A61F 2/0095* (2013.01); *A61L 27/3608* (2013.01); *A61L 27/3616* (2013.01);
(Continued)

(58) Field of Classification Search
CPC .... A61F 2/0095; A61L 27/3616; A61L 27/54; A61L 27/3608; A61L 2300/406; B65D 75/326
(Continued)

(56) References Cited

U.S. PATENT DOCUMENTS 2,022,906 A    12/1935  Weeks
2,981,405 A    4/1961   Grasty
(Continued)

FOREIGN PATENT DOCUMENTS

DE    19725499    12/1998
EP    1943975     7/2008

OTHER PUBLICATIONS

Non-Final Office Action for Design U.S. Appl. No. 29/590,395, dated Apr. 3, 2018.
(Continued)

*Primary Examiner* — Chun Hoi Cheung
*Assistant Examiner* — Brijesh V. Patel
(74) *Attorney, Agent, or Firm* — Marcella M. Bodner; Cole Schotz, P.C.

(57) ABSTRACT

A medical implant packaging assembly having an outer tray, an inner tray and a retainer. An implant which may include a hydrated tissue graft may be positioned within the packaging assembly. The inner tray is formed from a moisture barrier material whereby the implant may be maintained in a hydrated state, even if the implant is not immersed in fluid within the packaging assembly, thereby avoiding need for rehydrating steps that are required for dehydrated and/or cryopreserved implants prior to or during surgery. The outer tray and inner tray and a retainer are also made of transparent materials, enabling medical personnel to view the implant through these packaging components prior to and during surgery.

14 Claims, 6 Drawing Sheets

(51) Int. Cl.
*A61L 27/36* (2006.01)
*A61L 27/54* (2006.01)

(52) U.S. Cl.
CPC ............ *A61L 27/54* (2013.01); *B65D 75/326* (2013.01); *A61L 2300/406* (2013.01)

(58) Field of Classification Search
USPC ....... 206/438, 363, 592, 204, 210, 439, 776, 206/828; 53/467, 285, 432, 492, 425
See application file for complete search history.

(56) References Cited

U.S. PATENT DOCUMENTS

| | | | |
|---|---|---|---|
| 3,346,168 | A | 10/1967 | Rouder |
| D216,171 | S | 11/1969 | Murr |
| 3,776,411 | A | 12/1973 | Luckadoo |
| 4,046,311 | A | 9/1977 | Voytko |
| 4,391,863 | A | 7/1983 | Bonis |
| 4,674,676 | A | 6/1987 | Ferrara, Jr. et al. |
| 4,697,703 | A | 10/1987 | Will |
| 4,714,595 | A | 12/1987 | Anthony et al. |
| 4,736,850 | A | 4/1988 | Bowman et al. |
| 4,750,619 | A | 6/1988 | Cohen et al. |
| 4,763,791 | A | 8/1988 | Halverson et al. |
| D299,955 | S | 2/1989 | Kendrick |
| 4,850,488 | A | 7/1989 | Humbert |
| 4,863,052 | A | 9/1989 | Lambert |
| 4,867,372 | A | 9/1989 | Patterson |
| D305,478 | S | 1/1990 | Lahm et al. |
| 5,040,677 | A | 8/1991 | Tubo et al. |
| 5,176,258 | A | 1/1993 | Antal |
| 5,193,679 | A | 3/1993 | White |
| 5,257,692 | A | 11/1993 | Heacox |
| 5,494,162 | A | 2/1996 | Treace et al. |
| 5,503,324 | A | 4/1996 | Bacchetti et al. |
| D371,047 | S | 6/1996 | Houyou |
| 5,615,770 | A | 4/1997 | Applebaum et al. |
| 5,645,527 | A | 7/1997 | Beck |
| 5,690,226 | A | 11/1997 | N'Guyen |
| 5,720,391 | A | 2/1998 | Dohm et al. |
| 5,772,031 | A | 6/1998 | Landis |
| 5,868,253 | A | 2/1999 | Krueger et al. |
| 5,924,625 | A | 7/1999 | Klein et al. |
| 5,954,202 | A | 9/1999 | Mellon |
| 6,012,580 | A | 1/2000 | Peters et al. |
| 6,039,183 | A | 3/2000 | Rudnick et al. |
| D444,060 | S | 6/2001 | Eisner |
| D447,946 | S | 9/2001 | Tsurushi et al. |
| D450,240 | S | 11/2001 | Haag et al. |
| 6,622,864 | B1 | 9/2003 | Debbs et al. |
| 6,629,602 | B1 | 10/2003 | Heyman |
| 6,830,149 | B2 | 12/2004 | Merboth et al. |
| 6,854,599 | B2 | 2/2005 | Ferrara |
| D510,262 | S | 10/2005 | Isono |
| D510,263 | S | 10/2005 | Isono et al. |
| 7,162,850 | B2 | 1/2007 | Marino et al. |
| 7,316,318 | B1 | 1/2008 | Rosten et al. |
| 7,320,404 | B2 | 1/2008 | Landis |
| D598,282 | S | 8/2009 | Abrahamsson |
| 7,648,030 | B2 | 1/2010 | Landis |
| D612,594 | S | 3/2010 | Wade |
| 7,669,716 | B2 | 3/2010 | Lightner et al. |
| D613,418 | S | 4/2010 | Ryan |
| D638,137 | S | 5/2011 | Gross |
| D642,904 | S | 8/2011 | Turvey |
| 8,006,839 | B2 | 8/2011 | Hafner |
| 8,240,477 | B2 | 8/2012 | Lightner et al. |
| 8,365,910 | B2 | 2/2013 | Valaie et al. |
| D679,586 | S | 4/2013 | Afford et al. |
| D718,471 | S | 11/2014 | So et al. |
| D718,472 | S | 11/2014 | So |
| 8,893,883 | B2 | 11/2014 | Valaie et al. |
| 8,966,867 | B2 | 3/2015 | Liccardo et al. |
| 9,144,464 | B2 | 9/2015 | Knowlton et al. |
| D742,222 | S | 11/2015 | Liu |
| D755,986 | S | 5/2016 | Green |
| D766,368 | S | 9/2016 | Kiosky |
| D776,823 | S | 1/2017 | Duan-Arnold et al. |
| 9,851,349 | B2 | 12/2017 | Musat |
| D829,566 | S | 10/2018 | Safdie |
| D832,457 | S | 10/2018 | Poyss |
| D864,414 | S | 10/2019 | Poyss |
| 2002/0112981 | A1 | 8/2002 | Cooper et al. |
| 2003/0336781 | | 12/2003 | Liao |
| 2004/0132205 | A1 | 7/2004 | Moon |
| 2004/0224298 | A1 | 11/2004 | Brassil |
| 2005/0186373 | A1 | 8/2005 | Rhee et al. |
| 2005/0186376 | A1 | 8/2005 | Rhee et al. |
| 2005/0242017 | A1 | 11/2005 | Staats |
| 2005/0269231 | A1 | 12/2005 | White |
| 2010/0009459 | A1 | 1/2010 | Herminghaus |
| 2010/0155282 | A1 | 6/2010 | Govil |
| 2011/0139661 | A1 | 6/2011 | Ludwig |
| 2012/0021151 | A1 | 1/2012 | Tatarka et al. |
| 2012/0208273 | A1 | 8/2012 | Tarunina |
| 2013/0233736 | A1 | 9/2013 | Hess et al. |
| 2013/0327667 | A1 | 12/2013 | Grabowski |
| 2014/0073004 | A1 | 3/2014 | Williamson |
| 2014/0090999 | A1 | 4/2014 | Kirsch |
| 2014/0134302 | A1 | 5/2014 | Hodge |
| 2014/0135236 | A1 | 5/2014 | Musat |
| 2014/0202908 | A1 | 7/2014 | Liburd |
| 2014/0299498 | A1 | 10/2014 | Neal et al. |
| 2015/0076023 | A1 | 3/2015 | Kinyon |
| 2015/0259119 | A1 | 9/2015 | Duan-Arnold |
| 2015/0351893 | A1 | 12/2015 | Smith |
| 2016/0066998 | A1 | 3/2016 | Knowlton et al. |
| 2016/0135895 | A1 | 5/2016 | Faasse et al. |
| 2016/0166369 | A1 | 6/2016 | Anderson |
| 2016/0228231 | A1 | 8/2016 | Southard et al. |
| 2016/0324797 | A1 | 11/2016 | Allen |
| 2018/0263239 | A1 | 9/2018 | Sinclair et al. |

OTHER PUBLICATIONS

Non-Final Office Action for Design U.S. Appl. No. 29/619,999, dated Dec. 10, 2018.
Non-Final Office Action for U.S. Appl. No. 15/402,806, dated Sep. 11, 2019.
Office Action for U.S. Appl. No. 15/913,448 dated Feb. 6, 2019.
Office Action for U.S. Appl. No. 15/913,448, dated Aug. 6, 2019.
Restriction Requirement for U.S. Appl. No. 15/402,806, dated May 2, 2019.
U.S Appl. No. 15/913,448, filed Mar. 6, 2018.
Utility U.S. Appl. No. 15/402,806, filed Jan. 10, 2017.
Non-Final Office Action for U.S. Appl. No. 15/913,448, dated Aug. 6, 2019.
Non-Final Office Action for U.S. Appl. No. 15/913,448, dated Feb. 6, 2019.

IMPLANT PACKAGING ASSEMBLY

CROSS-REFERENCE TO RELATED APPLICATIONS

The present application claims the benefit of U.S. Non-Provisional patent application Ser. No. 15/913,448 filed on Mar. 6, 2018, issued as U.S. Pat. No. 10,582,994, on Mar. 10, 2020, the entire disclosure of which is hereby incorporated by reference herein.

FIELD OF THE INVENTION

The present invention relates generally to medical implant packaging, and in particular, to a packaging assembly for hydrated tissue grafts.

SUMMARY OF THE INVENTION

The present invention is directed to an implant packaging assembly, and specifically, packaging for hydrated tissue grafts. The packaging assembly comprises a package which includes an outer tray having a first cavity and formed from a first transparent material, an outer lid correspondingly-dimensioned with the outer tray, an inner tray having a second cavity, an inner lid made from a moisture barrier material and correspondingly-dimensioned with the inner tray, and a retainer. The inner tray is dimensioned to fit within the first cavity of the outer tray and formed from a second transparent material that is a moisture barrier. The inner tray thereby maintains a hydrated tissue graft in a hydrated state even when an implant, which comprises the hydrated tissue graft and is positioned in the second cavity, is not immersed in fluid. The retainer is dimensioned to receive the implant and fit within the second cavity of the inner tray so as to immobilize the implant therein.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

DETAILED DESCRIPTION OF THE INVENTION

Detailed embodiments of the present invention are disclosed herein. It should be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, and some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as examples for teaching one skilled in the art to variously employ the present invention.

The present invention generally relates to an implant packaging assembly for the storage, containment and transportation of medical implants, including tissue grafts (e.g., allografts, autografts, xenografts, tissue-engineered grafts, etc.). In one embodiment, the packaging assembly is specifically designed for tissue grafts that are hydrated (i.e., tissue grafts that are maintained in solution), but not immersed in fluid. Hydrated tissue grafts are ready to use when delivered to the surgical facility (e.g., hospital), which greatly simplifies preparation at the surgical site by avoiding the rehydrating steps that are required with dehydrated and/or cryopreserved tissue grafts. The hydrated grafts may be stored at room temperature, thereby avoiding the need for cryopreservation and/or refrigeration. The packaging assembly of the present invention and its components are described below.

Figure 1:
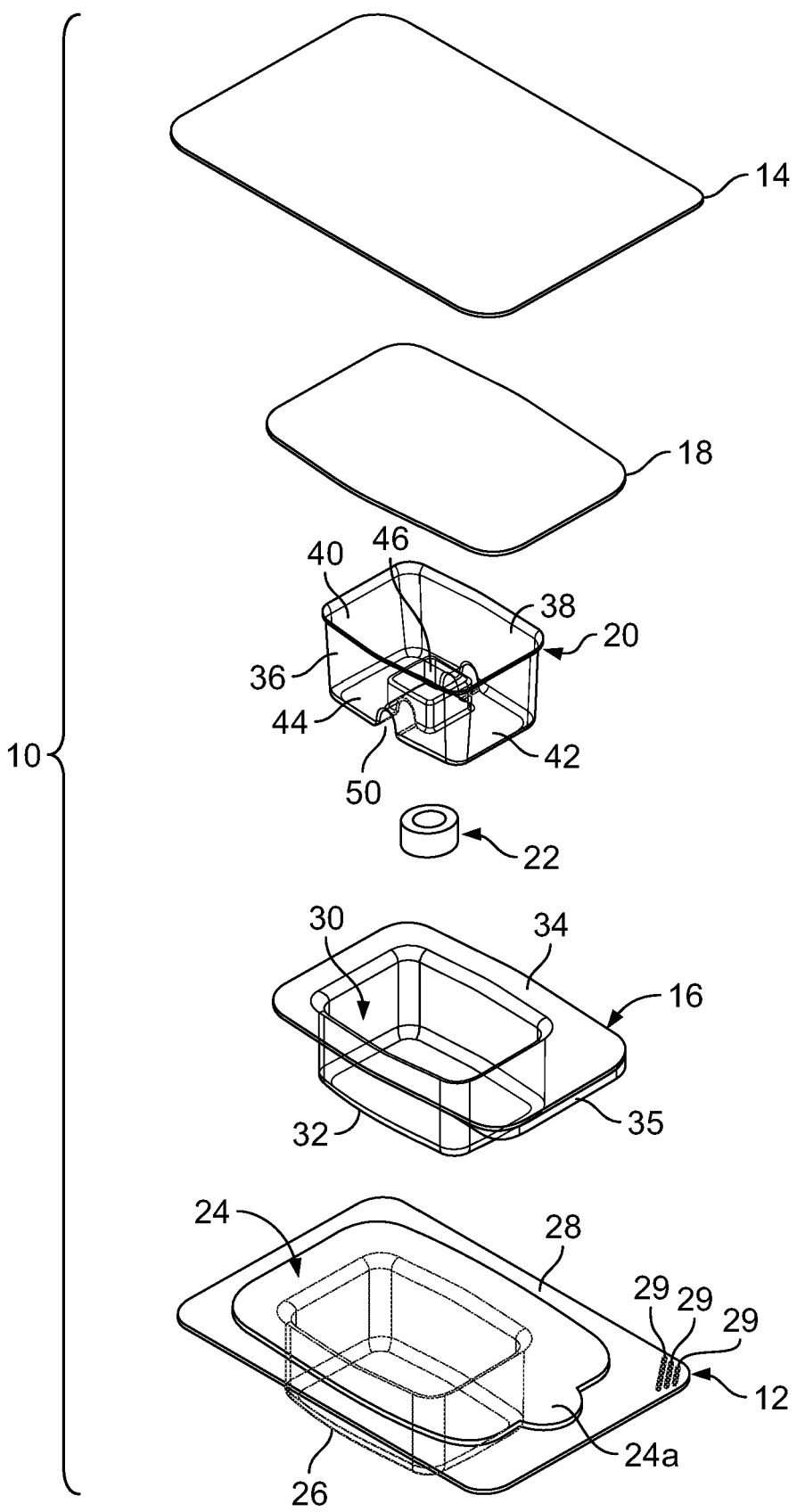
FIG. 1 is a perspective, exploded view of trays, lids and a retainer of the implant packaging assembly and an implant in connection with an embodiment of the present invention.
Figure 2:
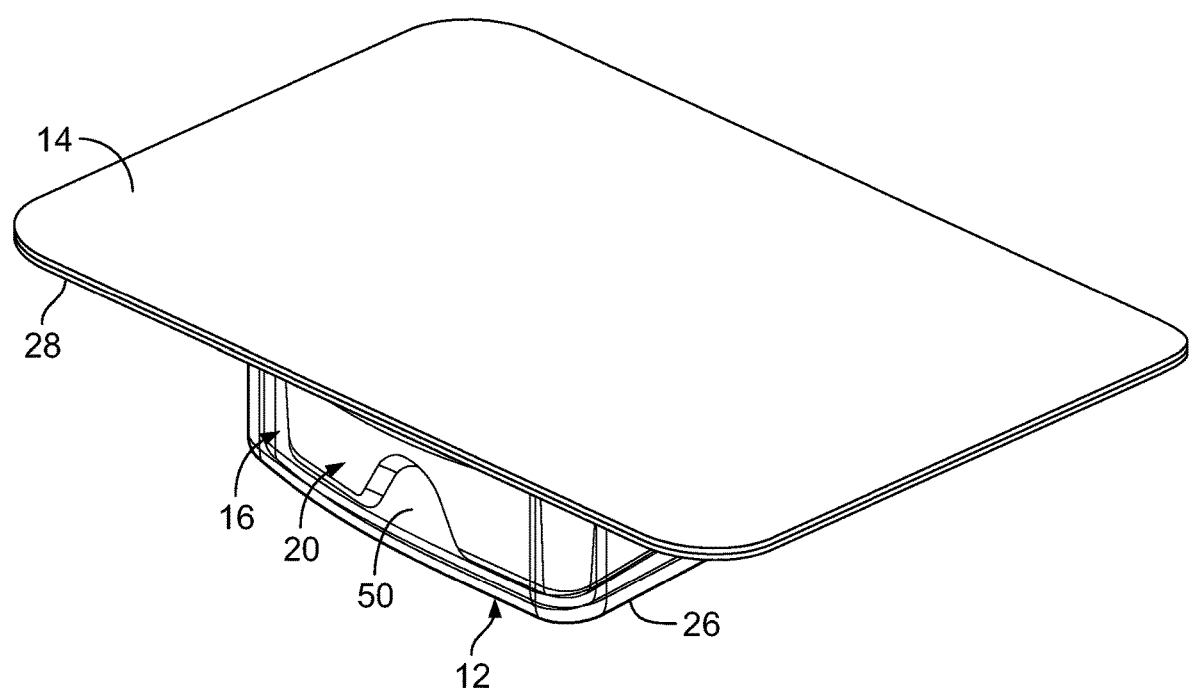
FIG. 2 is a perspective view of the trays, lids and retainer of FIG. 1, as assembled according to the present invention.

An embodiment of the packaging assembly 10 of the present invention is shown in FIGS. 1 and 2, and includes an outer tray 12, a correspondingly-dimensioned outer lid 14, an inner tray 16, a correspondingly-dimensioned inner lid 18 and a retainer 20, all of which constitute a package, and an implant 22, including a tissue graft.

The outer tray 12 includes a first cavity 24 formed inside of a first well, or base, 26, and a first rim, or flange, 28 circumferentially engaging the first base 26 and bordering the first cavity 24. In one embodiment, the first base 26 and first flange 28 of the outer tray 12 are formed monolithically in a generally rectangular shape, with the dimensions of the first flange 28 being larger than the corresponding dimensions of the first base 26. In one embodiment, the first cavity 24 includes a rounded portion 24a that extends into the first flange 28, so as to facilitate removal of the inner tray 16 from the first cavity 24.

The outer tray 12 is formed from a first transparent material. A "transparent material" is defined herein as a material having the property of transmitting light without appreciable scattering, so that objects lying beyond the material are seen clearly through the material (i.e., from the other side). The transparent material of the outer tray 12 enables a surgeon or other medical personnel to view the implant 22 through the outer tray 12 (and other transparent components of the assembly 10, further discussed below). In one embodiment, the first transparent material is PETG polymer, such as, for example, Pacur PETG. In one embodiment, the first transparent material is a moisture barrier material. In one embodiment, the first transparent material is a sterile barrier material. In one embodiment, the first transparent material is uncoated. In one embodiment, the outer tray 12 is thermoformed from the first transparent material.

In one embodiment, the thickness of the first transparent material forming the outer tray 12 is in a range of 0.01" to 0.1". In one embodiment, the nominal thickness of the first transparent material, prior to being formed into the outer tray 16, is 0.040".

Figure 5:
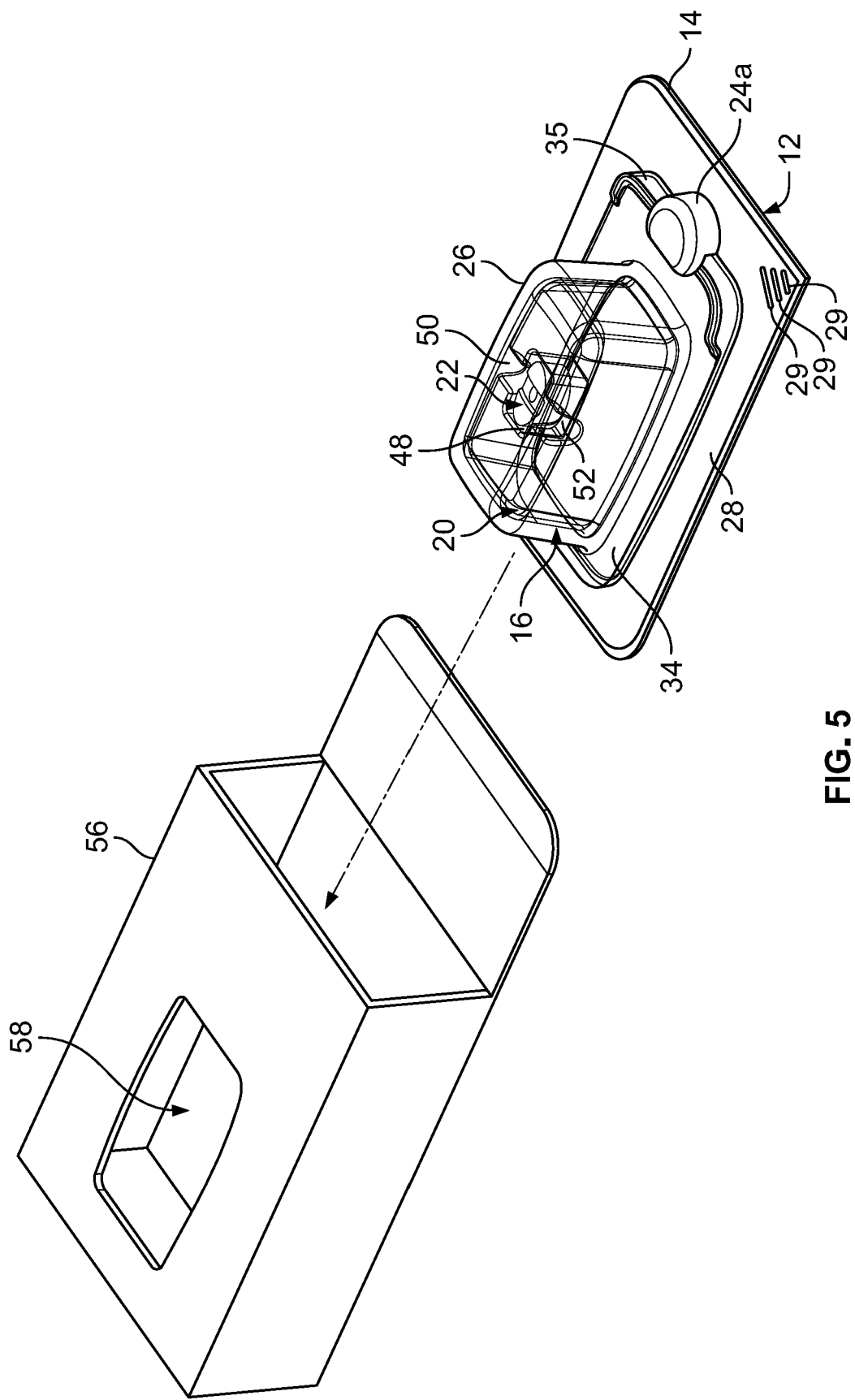
FIG. 5 is a perspective, exploded view of the implant packaging assembly of FIG. 1, and further including a carton.
Figure 6:
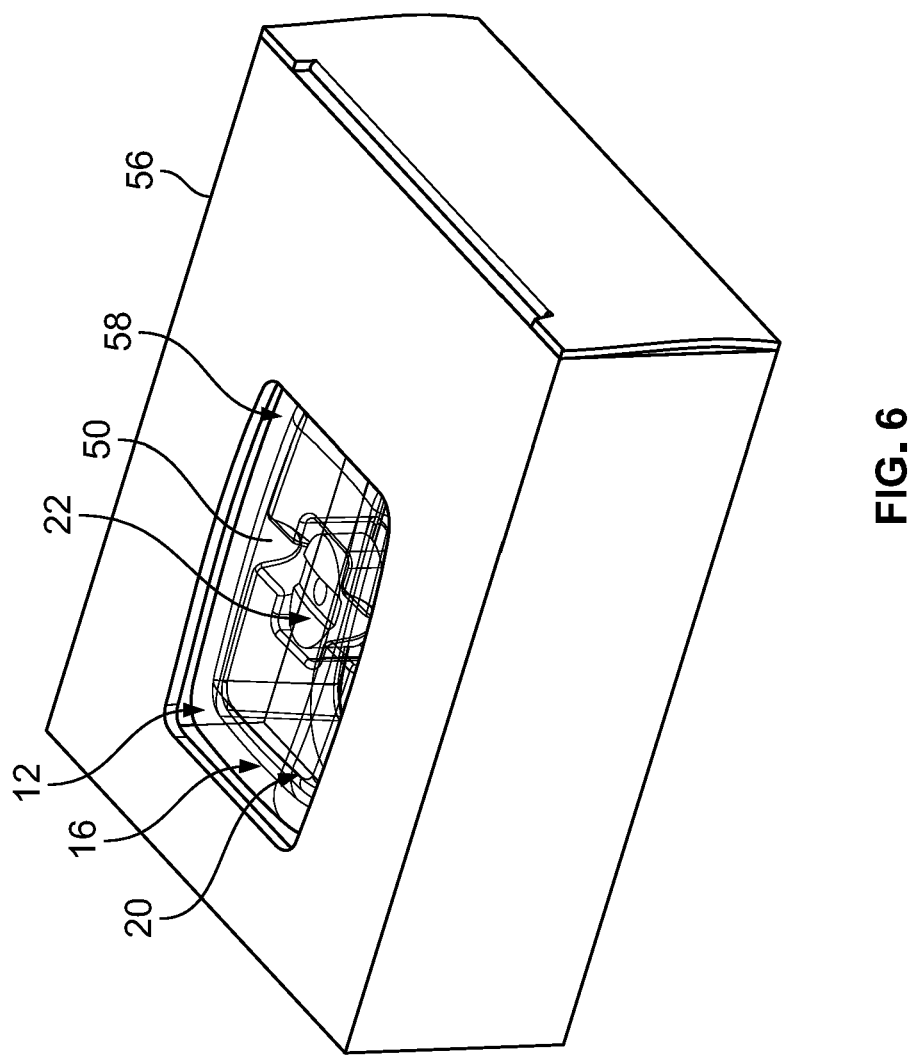
FIG. 6 is a perspective view of the implant packaging assembly of FIG. 5, as assembled according to the present invention.

The outer lid 14 is dimensioned to correspond to the first flange 28 of the outer tray 12. The outer lid 14 is formed to provide a first seal with the flange 28 when applied to same. In one embodiment, the first flange 28 includes a corner having a plurality of grooves 29 formed therein, which may be gripped by medical personnel (i.e., a surgeon) to facilitate removal of the outer lid 14 from the first flange 28. In one embodiment, three grooves 29 are provided in a parallel configuration on one corner of the first flange 28, as illustrated in FIGS. 1 and 5.

In one embodiment, the outer lid 14 is formed from a high-density polyethylene polymer. In one embodiment, the high-density polyethylene polymer is the one sold under the trademark TYVEK®.

Figure 3:
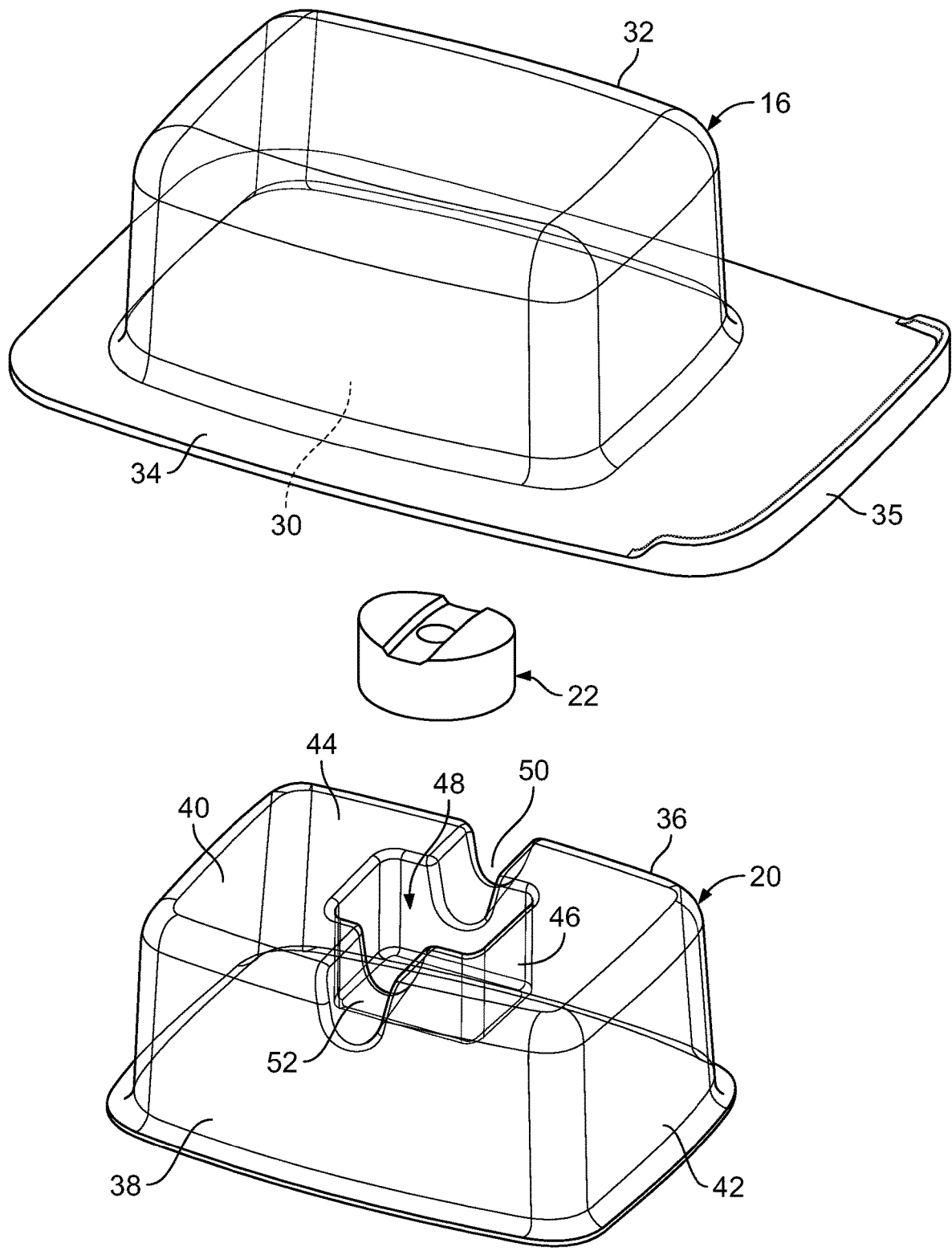
FIG. 3 is a perspective, exploded view of view of the inner tray and retainer of the implant packaging assembly and the implant of FIG. 1.
Figure 4:
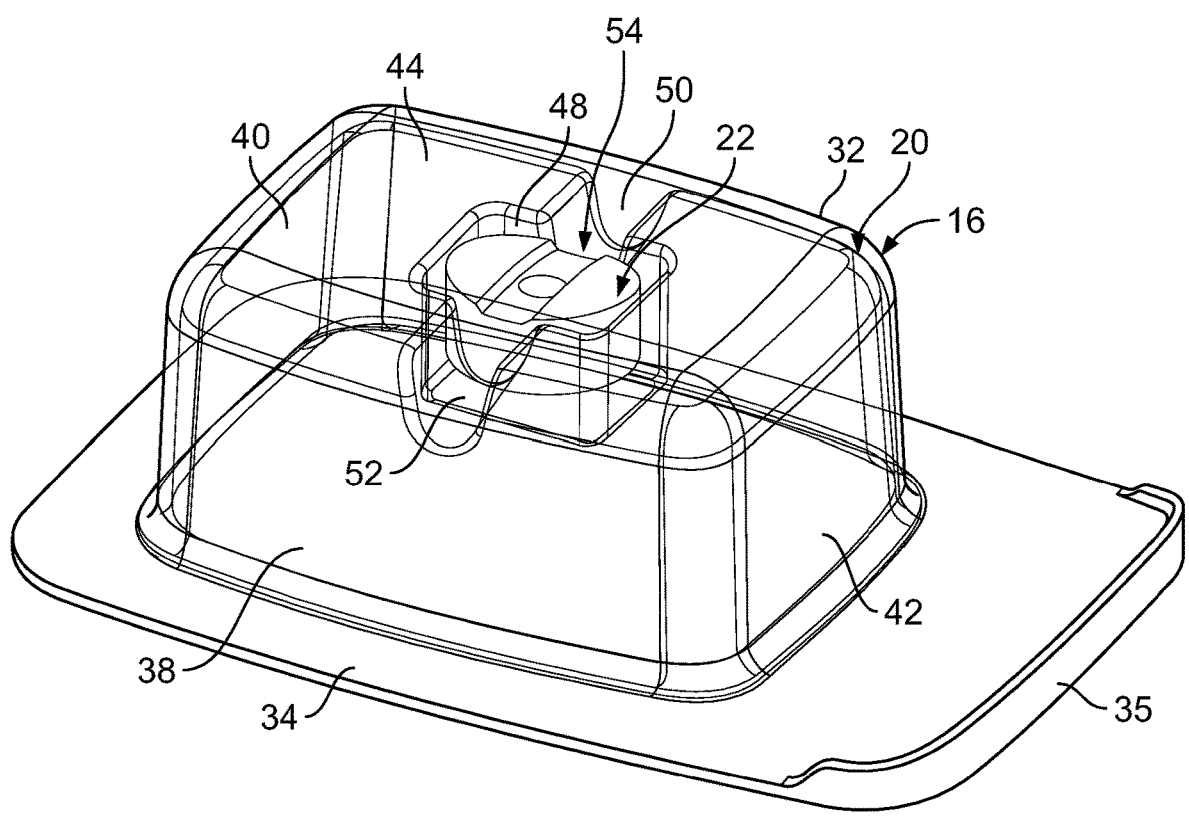
FIG. 4 is a perspective view of the inner tray, retainer and implant of FIG. 3, as assembled according to the present invention.

With continued reference to FIGS. 1 and 2, and also to FIGS. 3 and 4, the inner tray 16 includes a second cavity 30 formed inside of a second well, or base, 32, and a second rim, or flange, 34 circumferentially engaging the second base 32 and bordering the second cavity 30. In one embodiment, the second base 32 and second flange 34 of the inner tray 16 are formed monolithically in a generally rectangular shape, with the dimensions of the second flange 34 being larger than the corresponding dimensions of the second base 32.

In one embodiment, the second flange 34 includes a raised edge 35. The raised edge 35 extends in a generally perpendicular direction from a portion of the second flange 34 that corresponds to the location of the rounded portion 24a of the first cavity 24 of the outer tray 12, so as to facilitate removal of the inner tray 16 from the first cavity 24.

The inner tray 16 is dimensioned to fit within the first cavity 24 of the outer tray 12. In one embodiment, the first cavity 24 of the outer tray 12 includes two portions (not shown): a deeper first portion that is dimensioned to receive the second base 32 of the inner tray 16 therein, and a more shallow second portion, continuous with and surrounding the first portion, that is dimensioned to receive the second flange 34 of the outer tray 12 therein.

The inner tray 16 is formed from a second transparent material. The second transparent material enables a surgeon or other medical personnel to view the implant 22 through the inner tray 16.

The second transparent material is a sterile barrier and a moisture barrier, whereby the inner tray 16 maintains the implant 22, including a tissue graft in a hydrated state (referred to herein as the implant/tissue graft 22 for this embodiment). More particularly, the second material acts as a moisture barrier to the fluid (e.g., ethanol) that maintains the implant/tissue graft 22 in its hydrated state. In one embodiment, the second transparent material is a cyclo olefin polymer ("COP"), sold under the trademark ZEONEX®. In one embodiment, the inner tray 16 is formed from the second transparent material by injection molding.

In one embodiment, the thickness of the second transparent material forming the inner tray 16 is in a range of 0.01" to 0.1". In one embodiment, the nominal thickness of the second transparent material, prior to being formed into the inner tray 16, is 0.060".

The inner lid 18 is dimensioned to correspond to the second flange 34 of the inner tray 16. The inner lid 18 is formed to provide a second seal with the second flange 34 when applied to same.

In order to further provide a moisture barrier, the inner lid 18 is also made from a moisture barrier material in one embodiment. Such a material may include foil, such as aluminum foil. In one embodiment, the inner lid 18 includes an adhesive. In one embodiment, the inner lid 18 does not include an adhesive.

While the implant/tissue graft 22 is hydrated in a liquid, such as ethanol, the inner tray 16 is preferably not filled with the liquid, such that the implant/tissue graft 22 is hydrated, but not immersed in the liquid.

In one embodiment, the inner tray 16 is sterile. The sterility of the inner tray 16 (and the retainer 20 and implant/tissue graft 22 therein) may be maintained by keeping same sealed inside the outer tray 12 until after the packaging assembly 10 is introduced into the surgical field.

With continued reference to FIGS. 1, 3 and 4, the retainer 20 is formed in a generally rectangular shape, and includes two opposed sides 36, 38, two opposed ends 40, 42 and a generally planar base 44 formed so as to be generally perpendicular to the sides 36, 38 and ends 40, 42. The base 44 includes a depression 46 in which a third cavity 48 is formed. The third cavity 48 is dimensioned to receive the implant/tissue graft 22 therein. The third cavity 48 also functions as a reservoir in which a surgeon may mix blood, bone marrow aspirate (BMA) and/or any other fluid and further hydrate the implant/tissue graft 22 with such fluid(s) during surgery. The surgeon may also mix other substances with the implant/tissue graft 22 in the reservoir, including, for example, another tissue graft (e.g., an allograft), a filler and antibiotics.

The retainer 20 further includes two channels 50, 52 that are also formed in the base 44. The channels 50, 52 are continuous with the third cavity 48 of the retainer 20. One channel 50 extends between the third cavity 48 and one side 36 of the retainer 20, and the other channel 52 extends between the third cavity 48 and the other, opposite side 38 of the retainer 20. The channels 50, 52 facilitate the manipulation and removal of the tissue graft 22 from the third cavity 48 using a surgical instrument, as further described below.

The retainer 20 is dimensioned to securely fit within the second cavity 30 of the inner tray 16, wherein the third cavity 48 cooperates with an inner surface of the second base 32 of the inner tray 16 to form an enclosure 54 in which the implant/tissue graft 22 is securely contained and immobilized during transport and pre-surgery handling (see FIG. 4).

In one embodiment, the retainer 20 is sterile. The sterility of the retainer 20 (and implant/tissue graft 22 therein) may be maintained by keeping same sealed inside the sterile inner tray 16 (which is itself sealed inside the outer tray 12) until after the packaging assembly 10 is introduced into the surgical field.

The retainer 20 is formed from a third transparent material, which enables a surgeon or other medical personnel to view the implant/tissue graft 22 through the retainer 20. In one embodiment, the third transparent material is PETG polymer, such as, for example, Pacur PETG. In one embodiment, the third transparent material is uncoated. In one embodiment, the retainer 20 is thermoformed from the third transparent material.

In one embodiment, the thickness of the third transparent material forming the retainer 20 is in a range of 0.01" to 0.1". In one embodiment, the nominal thickness of the third transparent material, prior to be formed into the retainer, is 0.040".

Still referring to FIGS. 1, 3 and 4, the implant/tissue graft 22 is contained within the retainer 20, and within the enclosure 54 formed by the retainer 20 and the inner surface of the second base 32 of the inner tray 16, as described above. In various embodiments, the implant/tissue graft 22 may be an allograft, a xenograft or an autograft. In one embodiment, the implant/tissue graft 22 is made from bone. In other embodiments, the implant/tissue graft 22 is a made from a soft tissue, with non-limiting examples of soft tissue including skin, fascia, tendon, ligament, cartilage, muscle and placental tissues (i.e., amnion and/or chorion).

In the preferred embodiment, the implant/tissue graft 22 is hydrated in a liquid, such as ethanol, but is not immersed in the liquid. In other words, the inner tray 16 is preferably not filled with the liquid, such that the implant/tissue graft 22 is not immersed in the liquid.

The operation of the packaging assembly 10 will now be described, with reference to FIGS. 1-6. In one embodiment, the implant/tissue graft 22, once sufficiently hydrated, is placed inside the third cavity 48 of the retainer 20 (see FIGS. 1 and 3). The retainer 20 is then placed into the second cavity 30 of the inner tray 16 so as to form the enclosure 54 with the inner surface of the second base 32 of the inner tray 16, wherein the implant/tissue graft 22 is contained within the enclosure 54 (see FIG. 4). The inner lid 18 is then secured to the second flange 34 of the inner tray 16, sealing the implant/tissue graft 22 and retainer 20 inside of the second cavity 30 and forming a moisture barrier (i.e., the first seal). The implant/tissue graft 22, retainer 20, inner tray 16 and inner lid 18 are all sterile.

In one embodiment, the inner lid 18 is sealed to the second flange 34 of the inner tray 16 via heat sealing. In other embodiments, the seal may be formed by an adhesive, induction sealing or other known sealing methods.

In an alternate embodiment, the implant/tissue graft 22, once sufficiently hydrated, is placed inside the second cavity 30 of the inner tray 16. The retainer 20 is then placed into the second cavity 30 of the inner tray 16 on top of the implant/tissue graft 22 so as to form the enclosure 54 with the inner surface of the second base 32 of the inner tray 16, wherein the implant/tissue graft 22 is contained within the enclosure 54 (see FIG. 4).

Once sealed, the inner tray 16/inner lid 18 is placed into the first cavity 24 of the outer tray 12. The outer lid 14 is then secured to the first flange 28 of the outer tray 12, sealing the sealed inner tray 16/inner lid 18 therein (i.e., the second seal) (see FIG. 2).

In one embodiment, the outer lid 14 is sealed to the first flange 28 of the outer tray 12 via heat sealing. In other embodiments, the seal may be formed by an adhesive, induction sealing or other known sealing methods.

Once the outer lid 14 is secured to the first flange 28 of the outer tray 12, the outer tray 12/outer lid 14 is inserted into a carton 56 that is dimensioned to receive the assembled outer tray 12/outer lid 14 therein (see FIG. 5). In one embodiment, the carton 56 includes an opening, or window, 58 (see FIG. 6), wherein the implant/tissue graft 22 is visible through the transparent materials of the retainer 20, inner tray 16 and outer tray 12, as well as through the opening 58. While shown as rectangular in the figures, the opening 58 may be of any size and shape that enables medical personnel (i.e., the surgeon) to see the implant/tissue graft 22 through the opening 58. Once the outer tray 12/outer lid 14 is inserted into the carton 56, the carton 56 is closed (see FIG. 6) and the entire packaging assembly 10 is stored until it is transported to a hospital or other surgical facility for use. One or more instruction pamphlets and/or other package inserts (not shown) may be included inside the carton 56. Further, the carton 56 may include labels with instructions and/or Identification indicia (not shown).

Once the packaging assembly 10 is delivered to the hospital or other surgical facility, it is made available to medical personnel for a surgical procedure along with other surgical supplies. At the time of surgery, and the outer tray 12/outer lid 14 is removed from the carton 56. The outer lid 14 is removed from the outer tray 12 (i.e., the first flange 28), as facilitated by the corner grooves 29, thereby breaking the second seal formed by the outer lid 14. The inner tray 16/inner lid 18 is then removed from the first cavity 24 of the outer tray 12, as facilitated by the rounded portion 24a thereof and the edge 35 of the inner tray 16, and may be passed into a sterile surgical field. In another embodiment, the outer tray 12 may be inverted, thereby flipping the inner tray 16 onto a surface of the sterile surgical field.

Next, the inner lid 18 is removed from the inner tray 16, thereby breaking the first seal formed by the inner lid 18. In one embodiment, the inner tray 16 is then inverted and placed on a flat surface in the sterile surgical field, as illustrated in FIG. 4. The inner tray 16 may then be lifted off of/away from the retainer 20 to open the enclosure 54 and thereby expose the implant/tissue graft 22. In an alternate embodiment, the retainer 20 is removed from the second cavity 30 of the inner tray 16 to expose the implant/tissue graft 22, which may then be removed from the second cavity 30.

As discussed above, the surgeon may use the retainer 20 (i.e., the third cavity 48) as a reservoir in which to mix blood, bone marrow aspirate (BMA) and/or any other fluid and further hydrate the implant/tissue graft 22. The surgeon may also mix other substances with the implant/tissue graft 22 in the reservoir, including, for example, another tissue graft (e.g., allograft tissue), filler and/or antibiotics. When ready to remove the implant/tissue graft 22 from the retainer 20 (i.e., out of the third cavity 48), the surgeon may manipulate one or more appropriate surgical instruments (not shown) via channels 50 and/or 52 to engage the implant/tissue graft 22 and lift it out of the third cavity 48.

In other embodiments, the implant/tissue graft 22 may be used in a non-sterile, non-surgical area.

It will be understood that the embodiments described herein are merely exemplary and that a person of ordinary skill in the art may make many variations and modifications without departing from the spirit and scope of the invention. All such variations and modifications are intended to be included within the scope of the invention as defined in the appended claims. While not meant to be limiting, some of the possible variations and modifications are described below.

In alternate embodiments, the implant 22 is not a tissue graft, but made from a synthetic material, such as a polymer, metal/alloy or composite material. The implant 22 may also be a combination of a tissue graft and one or more synthetic materials.

In other alternate embodiments, the inner tray 16 may be partially or completely filled with liquid, such that the implant 22 is partially or completely immersed in fluid.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, temperature is in degrees centigrade.

Example 1—Bubble Emission Testing

Bubble emission testing was conducted on both the inner and outer trays, per ASTM F2096 (Standard Test Method for Detecting Gross Leaks in Packaging by Internal Pressurization (Bubble Test)), to verify the package integrity of both trays. All samples of the tested inner and outer trays passed the bubble emission testing.

Example 2—Moisture Barrier Testing by Moisture Loss of a Hydrated Sample

An initial evaluation for moisture barrier characteristics was conducted by storing samples of hydrated bone tissue grafts or other materials capable of being hydrated in fluid and contained in cyclo olefin polymer (COP) trays of a nominal thickness of 0.060" sealed to foil lids in an aging chamber set at 35° C., Relative Humidity 20%-25%, for 3, 6, 12 and 21 months real-time equivalent, and by calculating the percent weight change when compared with initial sample weight ($T_o$). The change in weight represents the moisture lost from the hydrated sample. The accelerated aging (AA) was performed per ASTM F1980 (Standard Guide for Accelerated Aging of Sterile Barrier Systems for Medical Devices).

The total sample weight at each timepoint was measured for eight (8) samples stored in control trays and lids (i.e., a tray formed from PETG with a lid formed from high-density polyethylene polymer (i.e., TYVEK®) lid sealed thereto), and for another eight (8) samples stored in trays formed from COP with a foil lid sealed thereto.

The results provided in Table 1 show that the COP trays sealed with the foil lid possess considerably better moisture barrier characteristics after exposure compared to the control tray/lid.

TABLE 1

| | Moisture Loss (% weight change) | | | |
|---|---|---|---|---|
| Material | 3 months | 6 months | 12 months | 21 months |
| 0.060" COP sealed to Foil | Mean = 0.00% St Dev = 0.00% | Mean = −0.10% St Dev = 0.00% | n/a | Mean = −1.00% St Dev = 0.24% |
| 0.040" PETG sealed to TYVEK ® polymer (control) | Mean = −5.78% St Dev = 1.42% | Mean = −10.80% St Dev = 2.68% | Mean = −20.30% St Dev = 4.71% | n/a |

Example 3—Moisture Barrier Testing by Water Vapor Transmission Rate (WVTR)

Moisture barrier characteristics were also measured by WVTR per ASTM 7709-12 Standard Test Methods for Measuring Water Vapor Transmission Rate (WVTR) of Pharmaceutical Bottles and Blisters. The test is a gravimetric method that measures the rate of weight gain as a result of water vapor transmission into the package which is absorbed by the desiccant inside the closed container. Samples of a COP tray formed from a nominal thickness of 0.060" and sealed to a foil lid and samples of a PETG tray formed from a nominal thickness of 0.040" prior to forming and sealed to a high-density polyethylene polymer (i.e., TYVEK®) lid resulted in average values shown in the Table 2. Results demonstrate the COP tray possesses considerably better moisture barrier properties compared to a PETG tray.

TABLE 2

| Material | WVTR (mg/cavity/day) |
|---|---|
| 0.060" COP sealed to Foil | Mean = 0.4397 St Dev = 0.045 |
| 0.040" PETG sealed to TYVEK ® polymer (control) | Mean = 91.4292 St Dev = 29.995 |

We claim:

1. An implant packaging assembly comprising a package which includes:
    an outer tray having a first cavity and formed from a first transparent material;
    an outer lid, the outer lid being correspondingly-dimensioned with the outer tray;
    an inner tray having a second cavity, the inner tray being dimensioned to fit within the first cavity of the outer tray, and formed from a second transparent material, the second material being a moisture barrier, whereby the inner tray maintains a hydrated tissue graft in a hydrated state even when an implant, which comprises the hydrated tissue graft and is positioned in the second cavity, is not immersed in fluid;
    an inner lid made from a moisture barrier material and being correspondingly-dimensioned with the inner tray; and
    a retainer, the retainer dimensioned to receive the implant and fit within the second cavity of the inner tray so as to immobilize the implant therein.

2. The implant packaging assembly of claim 1, wherein the moisture barrier material of the inner lid is a foil material.

3. The implant packaging assembly of claim 1, wherein the retainer is formed from a third transparent material.

4. The implant packaging assembly of claim 3, wherein the third transparent material is a PETG polymer.

5. The implant packaging assembly of claim 1, further comprising a carton, wherein the carton is dimensioned to receive the outer tray and outer lid therein, and wherein the carton includes an opening, whereby the implant is visible through the opening and the first and second transparent materials of the outer tray and inner tray.

6. The implant packaging assembly of claim 1, wherein the first transparent material is a PETG polymer.

7. The implant packaging assembly of claim 1, wherein the second transparent material is a cyclo olefin polymer.

8. The implant packaging assembly of claim 1, wherein the retainer includes a base having a depression forming a third cavity therein, the third cavity being dimensioned to receive the implant therein.

9. The implant packaging assembly of claim 8, wherein the third cavity is sized and shaped to function as a reservoir for mixing a fluid to further hydrate the tissue graft.

10. The implant packaging assembly of claim 9, wherein the fluid is selected from a group consisting of blood, bone marrow aspirate and a combination thereof.

11. The implant packaging assembly of claim 8, wherein the third cavity is sized and shaped to function as a reservoir for mixing a substance with the implant.

12. The implant packaging assembly of claim 11, wherein the substance is selected from: another tissue graft, filler, antibiotics and a combination thereof.

13. The implant packaging assembly of claim 8, wherein the retainer includes two channels formed in the base so as to be continuous with the third cavity.

14. The implant packaging assembly of claim 8, wherein the third cavity cooperates with an inner surface of the inner tray to form an enclosure in which the implant is securely contained and immobilized.

\* \* \* \* \*